United States Patent [19]

Brown

[11] 4,032,537
[45] June 28, 1977

[54] INDOLOTHIOPYRONES

[75] Inventor: Richard E. Brown, East Hanover, N.J.

[73] Assignee: Warner-Lambert Company, Morris Plains, N.J.

[22] Filed: May 10, 1976

[21] Appl. No.: 684,618

Related U.S. Application Data

[62] Division of Ser. No. 468,349, May 9, 1974, Pat. No. 3,971,806.

[52] U.S. Cl. .................................. 260/326.12 R
[51] Int. Cl.² .................................. C07D 209/04
[58] Field of Search .......................... 260/326.12 R

[56] References Cited

OTHER PUBLICATIONS

Grant et al., Journ. Amer. Chem. Soc., vol. 82, pp. 2742–2744 (1960).

*Primary Examiner*—Ethel G. Love
*Attorney, Agent, or Firm*—Albert H. Graddis; Frank S. Chow; Anne M. Kelly

[57] ABSTRACT

This invention relates to novel indolothiopyrones having the formula:

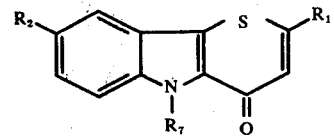

wherein $R_1$ is hydrogen, lower alkyl or aryl; $R_2$ is hydrogen or halogen; and $R_7$ is hydrogen, lower alkyl, lower alkenyl, lower alkynyl, nitro-substituted-aryl, or ω-substituted lower alkyl wherein the substituent is:

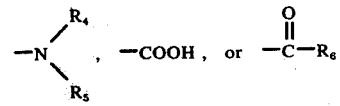

wherein $R_4$ and $R_5$ each represent hydrogen, lower alkyl, or together with the nitrogen atom, form a heterocyclic ring; and $R_6$ is lower alkoxy or amino, and novel intermediates used in their preparation. The indolothiopyrones are prepared by reacting a 3-mercaptoindole with sodium propiolate or a substituted sodium propiolate followed by acidification to obtain an intermediate acid; the intermediate acid cyclizes in the presence of an acid catalyst to obtain the indolothiopyrone structure which may be additionally subjected to halogenation, alkylation or hydrolysis to obtain derivatives having the various substituent groups disclosed. The compounds of this invention are useful in the treatment of angina pectoris and conditions benefitting from the depression of the central nervous system.

5 Claims, No Drawings

INDOLOTHIOPYRONES

This is a division of application Ser. No. 468,349 filed May 9, 1974, now U.S. Pat. No. 3,971,806.

DESCRIPTION OF THE INVENTION

The present invention relates to novel indolothiopyrones having the following formula:

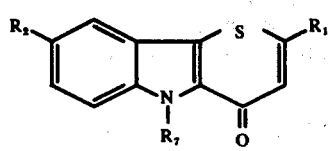

wherein $R_1$ is hydrogen, lower alkyl or aryl; $R_2$ is hydrogen or halogen; and $R_7$ is hydrogen, lower alkyl, lower alkenyl, lower alkynyl, nitro-substiuted-aryl, or ω-substituted lower alkyl wherein the substituent is:

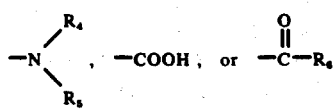

wherein $R_4$ and $R_5$ each represent hydrogen, lower alkyl, or together with the nitrogen atom, form a heterocyclic ring; and $R_6$ is lower alkoxy or amino.

This invention also includes within its scope a novel process for preparing the above compounds, as well as the intermediates employed in their synthesis.

The novel indolothiopyrones of this invention are obtained by a series of reactions which initially involve the preparation of a compound of the formula I:

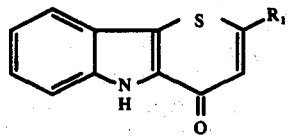

wherein $R_1$ is hydrogen, lower alkyl or aryl, by reacting a compound having the formula II:

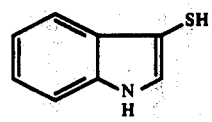

with a sodium propiolate or a substituted sodium propiolate having the formula

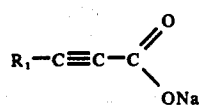

wherein $R_1$ is as defined above, to obtain, after acidification with a mineral acid, an intermediate acid having the formula III:

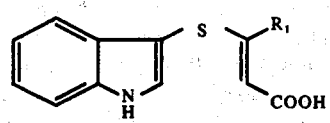

wherein $R_1$ is as defined above. This intermediate acid III is then cyclized with an acid catalyst such as sulfuric acid, trifluoroacetic acid, polyphosphoric acid and the like to give a cyclic product of structure I wherein $R_1$ is as defined above. Among the acid catalysts, polyphosphoric acid is preferred. The cyclized compound I is then subjected to a conventional direct halogenation reaction utilizing, for example, bromine or chlorine as the halogenating agent, to obtain a compound of the formula IV:

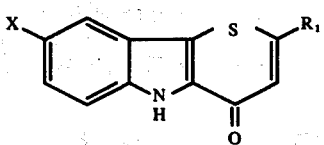

wherein X is halogen, and $R_1$ is hydrogen, lower alkyl, or aryl. Either compound I or halogenated compound IV may then be subjected to a further reaction for alkylation of the ring nitrogen. This may be achieved by reacting compounds I or IV with a halide alkylating agent in the presence of a basic catalyst, such as sodium hydride or sodium amide and the like.

Thus, a compound having the formula V:

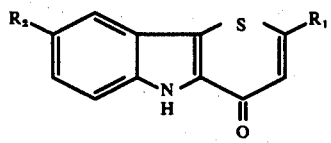

wherein $R_1$ is hydrogen, lower alkyl, or aryl and $R_2$ is hydrogen or halogen is reacted with an appropriate halide alkylating agent, in the presence of a basic catalyst, to obtain a compound having the formula VI:

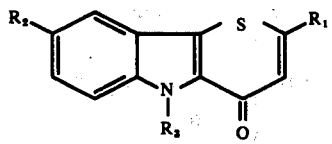

wherein $R_1$ and $R_2$ are as defined above and $R_3$ is lower alkyl, lower alkenyl, lower alkynyl, nitro-substituted-aryl, or ω-substituted lower alkyl wherein the substituent is:

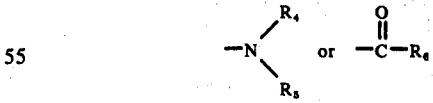

wherein $R_4$ and $R_5$ each represent hydrogen, lower alkyl, or together with the nitrogen atom, form a heterocyclic ring; and $R_6$ is lower alkoxy or amino.

Suitable alkylating agents which may be used in the abovementioned alkylation reaction include ortho- or para-nitro substituted aryl halide, such as ortho-nitrobenzene halide; or paranitrobenzene halide; lower alkyl halide, lower alkenyl halide, lower alkynyl halide, or ω-substituted-lower alkyl halide wherein the substituent is

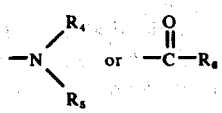

wherein $R_4$ and $R_5$ each represent hydrogen, lower alkyl, or together with the nitrogen atom, form a heterocyclic ring, and $R_6$ is lower alkoxy or amino, in the presence of a basic catalyst.

Compounds having the formula VI wherein the $R_3$ substituent has a terminal carboxylic acid ester function may be further subjected to hydrolysis to obtain a terminal carboxylic acid function on the $R_3$ substituent. Thus, a compound having the formula VII:

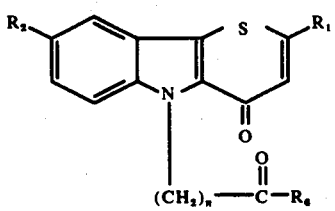

wherein $R_1$ is hydrogen, lower alkyl, or aryl; $R_2$ is hydrogen or halogen; $n$ is an integer from 1 to 5; and $R_6$ is lower alkoxy; is subjected to acid or basic hydrolysis to obtain a compound of the formula VIII:

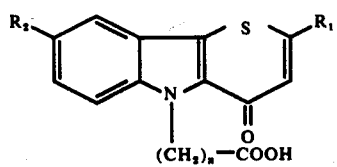

wherein $n$, $R_1$ and $R_2$ are as defined above. Basic hydrolysis conditions are preferred.

The final compounds obtained by the above series of reactions have the general formula IX:

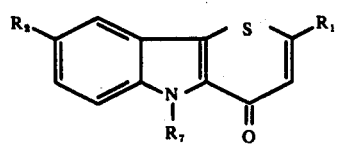

wherein $R_1$ is hydrogen, lower alkyl or aryl; $R_2$ is hydrogen or halogen; and $R_7$ is hydrogen, lower alkyl, lower alkenyl, lower alkynyl, nitro-substituted-aryl, or ω-substituted lower alkyl wherein the substituent is:

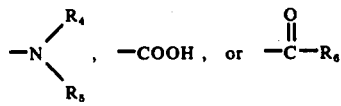

wherein $R_4$ and $R_5$ each represent hydrogen, lower alkyl, or together with the nitrogen atom, form a heterocyclic ring; and $R_6$ is lower alkoxy or amino.

Among the preferred final compounds of the invention are those indolothiopyrones of the formula IX wherein $R_1$ is hydrogen, 1 to 4 carbon lower alkyl or phenyl; $R_2$ is hydrogen or halogen; and $R_7$ is hydrogen, 1 to 4 carbon lower alkyl, 3 to 4 carbon lower alkenyl, 3 to 4 carbon lower alkynyl; nitro-substituted phenyl; or 1 to 4 carbon lower alkyl wherein the substitutent is (mono-loweralkyl)amino, lower dialkylamino, morpholino, piperidino, pyrrolidino, carboxyl or lower alkoxycarbonyl, wherein the lower alkyl and lower alkoxy groups each have 1 to 4 carbon atoms. Especially preferred compounds are those having formula IX wherein $R_1$ is hydrogen, methyl, or phenyl; $R_2$ is hydrogen, chloro or bromo; and $R_7$ is hydrogen, methyl, ethyl, propyl, isopropyl, allyl, propargyl, o-nitrophenyl, morpholinoethyl, (dimethylamino)propyl, carboxymethyl, (ethoxycarbonyl)methyl.

The acid intermediates of the formula III:

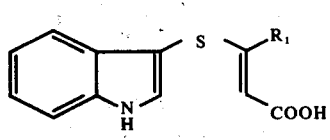

wherein $R_1$ represents hydrogen, lower alkyl or aryl are also novel and therefore within the scope of this invention. Compounds wherein $R_1$ is hydrogen, methyl or phenyl are especially preferred.

The starting materials for preparing the indolothiopyrones of the invention are readily available: for example, the 3-mercaptoindole of the formula II:

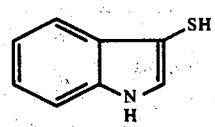

is reported in Paris, R. L. N., Tetrahedron Letters No. 51, p. 4465–4466, (1969). Sodium propiolate and substituted-sodium propiolates used in the process of this invention are commercially available or easily prepared by conventional methods.

The indolothiopyrones of formula IX are useful in the treatment of angina pectoris and in the treatment of conditions which require depression of the central nervous system. The indolothiopyrones of the invention may be administered to several mammalian species including rats, rabbits, dogs, pigs, monkeys and the like. For example, a dose of 1 to 20 mg/kg of body weight, when injected into the mammalian species, has been found to alleviate conditions associated with angina pectoris. Intravenous or intraduodenal injections of the indolothiopyrones of formula V in the dog at the above-mentioned dosage levels, compare favorably with the anti-anginal activity of nitroglycerin when tested in the coronary segmental resistance screen, according to the method described in M. M. Winbury et al., J. Pharm. Exp. Therap. 168: 70–95 (1969). The indolothiopyrones having formula V also display anti-anginal activity when administered in oral or sub-lingual dosage forms.

The indolothiopyrones of this invention are active, when injected intravenously at levels of 5 to 50 mg/kg of body weight, in depressing the central nervous system of the above-mentioned mammalian species. Central nervous system responses are evidenced by active responses to the induced rat rage screen, described in J. V. Brady et al., J. Comp. Physiol. Psychol. 46: 339 (1953) and in R. D. Sofia, Life Sci. 8: 705 (1969).

In order to administer the indolothiopyrones of this invention, they may be formulated with standard pharmaceutical carriers such as lactose, mannitol, dicalcium phosphate and the like, into dosage forms such as tablets, capsules and the like. They can also be combined with parenterally acceptable vehicles such as polyethylene glycol, sesame oil, peanut oil or the like, for injectable dosage forms.

The above-described regimen can, of course, be varied with the severity of the condition and the weight, species, and sex of the mammal being treated by methods well known in the healing arts.

In all of the above structures the lower alkyl and lower alkoxy functions are meant to include alkyl groups having 1 to 6 carbon atoms in a straight or branched chain. Lower alkenyl and lower alkynyl groups are meant to include unsaturated alkyl chains having from 3 to 6 carbon atoms. In the preferred compounds of the invention, the alkyl and alkoxy groups have from 1 to 4 carbon atoms; the alkenyl and alkynyl groups have from 3 to 4 carbon atoms. Aryl groups are meant to include unsaturated cyclic hydrocarbons derived from benzene such as phenyl, naphthyl and the like. The nitro-substituted phenyl group may be an ortho- or para-nitrophenyl group. The alkylating agent used to form the nitro-substituted phenyl group may be an ortho- or para-nitrobenzene halide.

The following examples serve to illustrate the invention.

EXAMPLE 1

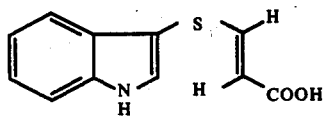

3-(Indol-3-ylthio)acrylic acid.

A mixture of 35.0 g (0.5 mole) of propiolic acid, 97 g (0.5 mole) of 3-mercaptoindole and 500 ml of 1N NaOH solution is stirred for 1 hour at 95° C. The solution is cooled and the precipitated solid washed with water and discarded. The filtrate is acidified with 4N HCl and the gummy precipitate extracted with ether. The ether is dried and evaporated and the residue recrystallized from 250 ml of acetonitrile to give 88 g of product, mp 172°–173° C.

Anal. Calcd. for $C_{11}H_9NO_2S$: C, 60.26; H, 4.13; N, 6.39; S, 14.62. Found: C, 60.07; H, 4.04; H, 6.30; S, 14.64.

EXAMPLE 2

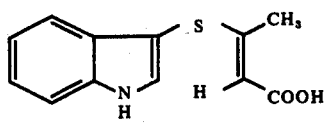

3-(Indol-3-ylthio)crotonic acid.

By the same method as described in Example 1, 0.2 mole each of 3-mercaptoindole and tetrolic acid gives 10.2 g of product after recrystallization from acetonitrile, mp 201°–202° C.

Anal. Calcd. for $C_{12}H_{11}NSO_2$: C, 61.78; H, 4.75; N, 6.00. Found: C, 62.04; H, 4.80; N, 5.92.

EXAMPLE 3

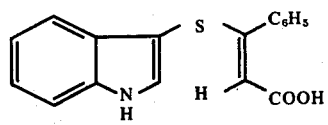

3-(Indol-3-ylthio)cinnamic acid.

By the same method as described in Example 1, 0.2 mole each of 3-mercaptoindole and phenylpropiolic acid gives 20.0 g of product after recrystallization from acetone-water, mp 165°–167° C.

Anal. Calcd. for $C_{17}H_{13}NSO_2$: C, 69.13; H, 4.44; N, 4.74. Found: C, 69.06; H, 4.61; N, 4.84.

EXAMPLE 4

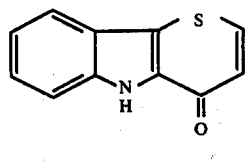

Thiopyrano[3,2-b]indol-4(5H)-one.

A solution of 76.7 g (0.35 mole) of 3-(indol-3 ylthio) acrylic acid in 4 liters of 10% polyphosphoric acid in acetic acid is stirred at room temperature for 65 hours. The supernatent is decanted from the sticky precipitate, which is partitioned between chloroform and 5% NaOH solution. The organic phase is washed with water, dried, evaporated and the residue recrystallized from 3 liters of 95% ethanol to give 37.8 g of product, mp 242°–243° C.

Anal. Calcd. for $C_{11}H_7NOS$: C, 65.65; H, 3.51; N, 6.96; S, 15.93. Found: C, 66.24; H, 3.45; N, 6.92; S, 15.80.

EXAMPLE 5

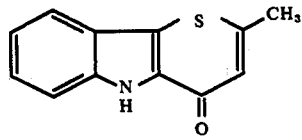

2-Methylthiopyrano[3,2-b]indol-4(5H)-one.

By the same method as described in Example 4, 9.45 g (0.04 mole) of β-(indol-3-ylthio) crotonic acid is cyclized to give 4.5 g of product afer recrystallization from ethanol, mp 295°–296° C.

Anal. Calcd. for $C_{12}H_9NOS$: C, 66.95; H, 4.21; N, 6.51. Found: C, 66.99; H, 4.32; N, 6.51.

EXAMPLE 6

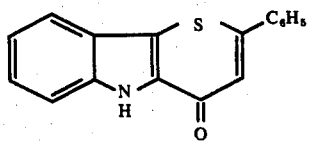

2-Phenylthiopyrano[3,2-b]indol-4(5H)-one.

By the same method as described in Example 4, 11.4 g of β-(indol-3-ylthio)cinnamic acid is cyclized to give 3.5 g of product after recrystallization from ethanol, mp 271°–272° C.

Anal. Calcd. for $C_{17}H_{11}NOS$: C, 73.62; H, 4.00; N, 5.05. Found: C, 73.35; H, 4.04; N, 5.07.

EXAMPLE 7

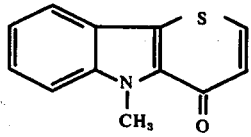

5-Methylthiopyrano[3,2-b]indol-4-(5H)-one.

Sodium hydride (2.3 g of 50% suspension in mineral oil, 0.05 mole) is washed with hexane and suspended in 25 ml of dimethylformamide (DMF). Thiopyrano [3,2-b]indol-4(5H)-one, 10.0 g (0.05 mole) in 130 ml of DMF is added and the mixture stirred for 3 hours. Methyl iodide (14.2 g, 0.1 mole) is added and the mixture stirred for 3 hours and then poured over ice. The white precipitate is filtered, dried and recrystallized from hexane to give 9.3 g of product, mp 113°–114° C.

Anal. Calcd. for $C_{12}H_9NOS$: C, 66.95; H, 4.21; N, 6.51; S, 14.89. Found: C, 67.18; H, 4.29; N, 6.53; S, 14.89.

EXAMPLE 8

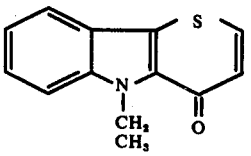

5-Ethylthiopyrano[3,2-b]indol-4(5H)-one.

By the same method as described in Example 7, 4.8 g of thiopyrano [3,2-b]-indol-4(5H)-one is alkylated with ethyl bromide to give 4.8 g of product, mp 103°–104° C, after recrystallization from methylene chloride-hexane.

Anal. Calcd. for $C_{13}H_{11}NOS$: C, 68.09; H, 4.84; N, 6.11. Found: C, 68.37; H, 4.95; N, 6.34.

EXAMPLE 9

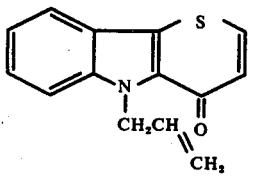

5-Allylthiopyrano[3,2-b]indol-4(5H)-one.

By the same method as described in Example 7, 4.8 g of thiopyrano [3,2-b]-indol-4(5H)-one is alkylated with allyl bromide to give 3.9 g of product, mp 67°–68° C, after recrystallization from methylene chloride-hexane.

Anal. Calcd. for $C_{14}H_{11}NOS$: C, 69.68; H, 4.59; N, 5.80. Found: C, 69.49; H, 4.59; N, 5.75.

EXAMPLE 10

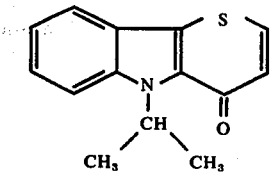

5-Isopropylthiopyrano[3,2-b]indol-4(5H)-one.

By the same method as described in Example 7, 4.8 g of thiopyrano-[3,2-b]indol-4(5H)-one is alkylated with isopropyl bromide to give 2.4 g of product, mp 154°–6° C, after recrystallization from methylene chloride-hexane.

Anal. Calcd. for $C_{14}H_{13}NOS$: C, 69.11; H, 5.39; N, 5.76. Found: C, 68.83; H, 5.37; N, 5.64.

EXAMPLE 11

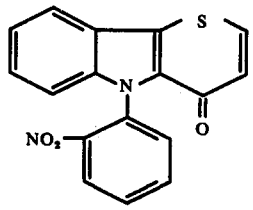

5-(o-nitrophenyl)thiopyrano[3,2-b]indol-4(5H)-one.

By the same method as described in Example 7, 8.9 g of thiopyrano [3,2-b]-indol-4(5H)-one is alkylated with o-fluoronitrobenzene, except the reaction is stirred for 40 hours at 95° C. The yield of product is 9.2 g, mp 207°–208° C after recrystallization from ether-hexane.

Anal. Calcd. for $C_{17}H_{10}N_2O_3S$: C, 63.35; H, 3.13; N, 8.69. Found: C, 63.37; H, 3.04; N, 8.55.

EXAMPLE 12

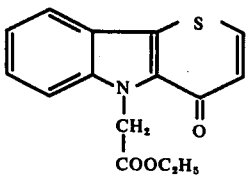

Ethyl 4,5-dihydro-4-oxothiopyrano[3,2-b]indol-5-acetate.

By the same method as described in Example 7, 4.8 g of thiopyrano-[3,2-b]indol-4(5H)-one is alkylated with ethyl bromoacetate to give 6.0 g of product, mp 163°–165° C, after recrystallization from ethyl acetate.

Anal. Calcd. for $C_{15}H_{13}NO_3S$: C, 62.70; H, 4.56; N, 4.87. Found: C, 62.67; H, 4.48; N, 5.12.

EXAMPLE 13

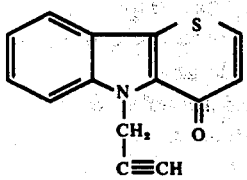

5-Propargylthiopyrano[3,2-b]indol-4(5H)-one.

By the same method as described in Example 7, 4.8 g of thiopyrano[3,2-b]indol-4(5H)-one is alkylated with propargyl bromide to give 5.0 g of product, mp 144° C after recrystallization from methylene chloride-ether.

Anal. Calcd. for $C_{14}H_9NOS$: C, 70.27; H, 3.79; N, 5.85. Found: C, 70.30; H, 3.82; N, 5.64.

EXAMPLE 14

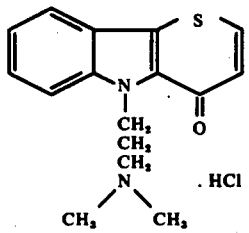

5-[3(Dimethylamino)propyl]thiopyrano[3,2-b]indol-4(5H)-one hydrochloride.

A mixture of 2.3 g (0.055 mole) of 50% sodium hydride in mineral oil, 50 ml of dimethylformamide (DMF) and 10.0 g (0.05 mole) of thiopyrano [3,2-b]indol-4(5H)-one is stirred for 3 hours, then 12.2 g (0.1 mole) of dimethylaminopropylchloride is added. Stirring is continued for 20 hours. at 95°, then the mixture is poured onto ice containing conc. HCl. The cloudy solution is clarified with charcoal, made basic with 20% sodium hydroxide solution, and the precipitated oil extracted with ether. The ether is dried, and dry HCl passed in. The precipitated salt weighed 10.1 g and is recrystallized from isopropanol, mp 226°-228° C.

Anal. Calcd. for $C_{16}H_{19}ClN_2OS$: C, 59.52; H, 5.93; N, 8.68; S, 9.93. Found: C, 59.82; H, 6.08; N, 8.49; S, 9.83.

EXAMPLE 15

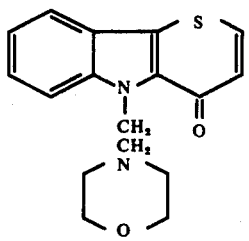

5-(2-Morpholinoethyl)thiopyrano[3,2-b]indol-4(5H)-one.

4.8 g of thiopyrano [3,2-b]indol-4(5H)-one and 15 g of chloroethylmorpholine, are reacted in the same manner as described in Example 14, except that the crude free base crystallized. This is filtered and recrystallized from methylenechloride-hexane to give 5.1 g of product, mp 136°-137° C.

Anal. Calcd. for $C_{17}H_{18}N_2O_2S$: C, 64.94; H, 5.77; N, 8.91. Found: C, 64.70; H, 5.73; N, 8.70.

EXAMPLE 16

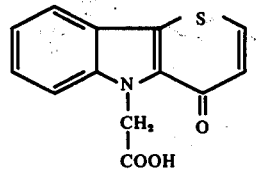

4,5-Dihydro-4-oxothiopyrano[3,2-b]indole-5-acetic acid.

A mixture of 6.0 g (0.021 mole) of ethyl 4,5-dihydro-4-.xothiopyrano[3,2-b]indole-5-acetate and 21 ml of 1N sodium hydroxide solution is stirred for one-half hour at 95° C. The clear solution is cooled, acidified and the solid filtered and recrystallized from isopropanol to give 4.9 g of product, mp 275°-278° C.

Anal. Calcd. for $C_{13}H_9NO_3S$: C, 60.22; H, 3.50; N, 5.40. Found: C, 60.16; H, 3.59; N, 5.36.

EXAMPLE 17

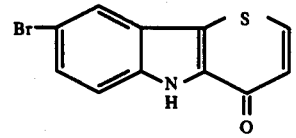

8-Bromothiopyrano[3,2-b]indol-4(5H)-one.

A solution of 8.04 g (0.04 mole) of thiopyrano[3,2-b]indol-4(5H)-one in 200 ml of acetic acid is treated dropwise with stirring at room temperature with 8.0 g (0.05 mole) of bromine. An immediately heavy precipitate formed. The mixture is concentrated to dryness and the solid residue suspended in 20 ml of pyridine and stirred for 10 minutes at 95°. The reaction mixture is poured onto ice, the solid is filtered and recrystallized from dimethylformamide, mp 334°-337° C.

Anal. Calcd. for $C_{11}H_6BrNOS$: C, 47.16; H, 2.16; N, 5.00; Br, 28.52. Found: C, 47.50; H, 2.32; N, 5.09; Br, 28.48.

EXAMPLE 18

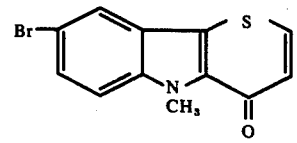

8-Bromo-5-methylthiopyrano[3,2-b]indol-4(5H)-one.

By the same manner as described in Example 7, 4.2 g (0.015 mole) of 8-bromothiopyrano[3,2-b]indol-4(5H)-one is methylated to give 2.85 g of product, mp 243°-244° C, after recrystallization from methylene chloride-hexane.

Anal. Calcd. for C$_{12}$H$_8$BrNOS: C, 49.00; H, 2.74; N, 4.76; Br, 27.16. Found: C, 49.2; H, 2.76; N, 4.74; Br, 27.12.

I claim:

1. A compound of the formula III:

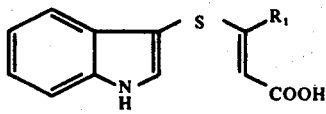

III wherein R$_1$ represents hydrogen, lower alkyl or aryl.

2. A compound according to claim 1 wherein R$_1$ is hydrogen, methyl or phenyl.

3. A compound according to claim 2 which is 3-(indol-3-ylthio)acrylic acid.

4. A compound according to claim 2 which is 3-(indol-3-ylthio)crotonic acid.

5. A compound according to claim 2 which is 3-(indol-3-ylthio)cinnamic acid.

* * * * *